US 6,731,437 B2

(12) United States Patent
Carrillo

(10) Patent No.: US 6,731,437 B2
(45) Date of Patent: May 4, 2004

(54) ENERGY BEAM GUIDE FOR AN ELECTROPHORESIS SYSTEM

(75) Inventor: Albert L. Carrillo, Redwood City, CA (US)

(73) Assignee: Applera Corporation, Foster City, CA (US)

( * ) Notice: Subject to any disclaimer, the term of this patent is extended or adjusted under 35 U.S.C. 154(b) by 197 days.

(21) Appl. No.: 09/849,380

(22) Filed: May 4, 2001

(65) Prior Publication Data

US 2002/0162746 A1 Nov. 7, 2002

(51) Int. Cl.⁷ ............. G02B 9/00; G02B 6/02; G02B 6/10; G02B 27/30
(52) U.S. Cl. .......... 359/796; 385/124; 385/146; 359/641
(58) Field of Search ............... 359/641, 796; 385/124, 146

(56) References Cited

U.S. PATENT DOCUMENTS

| | | | |
|---|---|---|---|
| 5,073,239 A | 12/1991 | Hjerten | 204/180.1 |
| 5,141,609 A | 8/1992 | Sweedler et al. | 204/180.1 |
| 5,439,578 A | 8/1995 | Dovichi et al. | 204/299 R |
| 5,529,679 A | 6/1996 | Takahashi et al. | 204/603 |
| 5,582,705 A | 12/1996 | Yeung et al. | 204/603 |
| 5,757,014 A | 5/1998 | Bruno et al. | 250/458.1 |
| 5,833,826 A | 11/1998 | Nordman | 204/452 |
| 5,938,908 A | 8/1999 | Anazawa et al. | 204/603 |
| 5,953,477 A * | 9/1999 | Wach et al. | 385/115 |
| 6,017,434 A | 1/2000 | Simpson et al. | 204/612 |
| 6,144,791 A * | 11/2000 | Wach et al. | 385/123 |

* cited by examiner

Primary Examiner—David N. Spector

(57) ABSTRACT

The energy beam guide comprises a first region having a first refractive index, the first region having an energy beam receiving end and an inclined first boundary opposing the energy beam receiving end. The energy beam guide also includes a second region having a second refractive index that is less than the first refractive index. The second region shares the first boundary with the first region, and has a declined second boundary opposing the first boundary. A predetermined distance separates the first and second boundaries. Finally, the energy beam guide comprises a third region having a third refractive index. The third region shares the second boundary with the second region. Also provided are a method for making and using the energy beam guide.

50 Claims, 9 Drawing Sheets

ENERGY BEAM GUIDE FOR AN ELECTROPHORESIS SYSTEM

TECHNICAL FIELD

The invention relates generally to an electrophoresis system. More particularly, the invention is directed to a detection cell for receiving a sample to be analyzed photometrically, where the detection cell acts as light guide for excitation light used to detect separated chemical components.

BACKGROUND OF THE INVENTION

In biotechnology, separation and analysis of chemical samples is critically important. Moreover, it is desirable to conduct multiple separations and analyses of the separated components simultaneously to increase the speed and efficiency at which chemical samples are evaluated. For example, separation technologies such as electrophoresis are used in DNA sequencing, protein molecular weight determination, genetic mapping, and other types of processes used to gather large amounts of analytical information about particular chemical samples.

One method used to separate chemical samples into their component parts is electrophoresis. Electrophoresis is the migration of charged colloidal particles or molecules through a solution under the influence of an applied electric field usually provided by immersed electrodes, where the colloidal particles are a suspension of finely divided particles in a continuous medium.

Historically, a polymer gel containing the finely divided particles is placed between two glass plates and an electric field applied to both ends of the plates. This method, however, offers a low level of automation and long analysis times.

More recently, the capillary electrophoresis (hereafter "CE") method was developed, which has the added advantages of speed, versatility and low running costs. Operation of a CE system involves application of a high voltage (typically 10–30 k V) across a narrow bore capillary (typically 25–100 μm). The capillary is filled with electrolyte solution which conducts current through the inside of the capillary. The ends of the capillary are dipped into reservoirs filled with the electrolyte. Electrodes made of an inert material such as platinum are also inserted into the electrolyte reservoirs to complete the electrical circuit. A small volume of sample is injected into one end of the capillary. The capillary passes through a detector, usually a UV absorbance detector, at the opposite end of the capillary. Application of a voltage causes movement of sample ions towards their appropriate electrode usually passing through the detector. Different sample ions arrive at a detection part of the capillary at different times. The sample may be labeled with a fluorescent marker so that when the sample passes through a beam of light at the detector, the fluorescent marker fluoresces and the fluorescence is detected as an electric signal. The intensity of the electric signal depends on the amount of fluorescent marker present in the detection zone. The plot of detector response with time is then generated which is termed an electropherogram.

CE is a particularly preferred separation method, as it allows the use of high electric fields, due to the capillary tube efficiently dissipating the resulting heat produced by the electric field. As such, the separations achieved are much better than the more traditional electrophoretic systems. In addition, multiple capillary tubes may be closely spaced together and used simultaneously to increase sample throughput.

In traditional CE systems, analysis or detection of the separated components is performed while the sample is still located within the capillary, and may be accomplished using photometric techniques such as adsorbance and fluorescence. Adsorbance and fluorescence is where excitation light is directed toward the capillary tube, and light emitted from the sample (e.g., fluorescence) is measured by a detector, thereby providing information about the separated components. Therefore, in these systems, excitation light directed at the sample, as well as light emitted from the sample, must be transmitted through the capillary's walls. A drawback of this approach is that the fused silica capillaries typically used in capillary electrophoresis are poor optical elements and cause significant scattering of light. The problem associated with light scattering is exacerbated by having multiple capillaries disposed side-by-side, as scattered excitation light from one capillary interferes with the detection of samples in neighboring capillaries.

One approach to solving the problem of on-capillary detection has been to detect a sample after the sample emerges from the capillary in a detection cell having superior optical characteristics, e.g., a flat quartz chamber. In this system, a sample is transported from the outlet of a capillary to the detection cell by electrophoresis under the influence of the same voltage difference used to conduct the electrophoretic separation. Examples of this type of system are disclosed in U.S. Pat. No. 5,529,679, which is incorporated herein by reference.

A variation of the above system replaces the capillary tubes with a series of parallel channels formed in a plate or chip, where the channels are in fluid communication with a detection cell in a manner similar to that described above. This type of system is known as a micro-channel array.

While addressing some of the abovementioned problems, the detection cell type CE system has drawbacks of its own. For example, excitation energy, such as light from a laser, has the tendency to scatter, thereby diminishing the energy's intensity as it transmitted through the detection cell.

A partial cross-section of a prior art detection cell 102 is shown in FIG. 1A. The detection cell 102, typically made from glass, forms a cavity 108, which is filled with an electrolytic polymer 110 containing a sample to be detected. Rays of light 104, typically from a laser, enter the detection cell 102 at a first end 112. Because the first end 112 is normal to the rays of light 104, the light 104 does not scatter, i.e., reflect or refract, when passing into the detection cell, from air to glass. However, when the light 104 passes through the boundary 106 between the detection cell and the polymer 110, the light is refracted. This is due to the angle or slope of the boundary 106, and the difference in refractive indices of the glass and polymer. The angle or slope of the boundary 106 is caused by current etching and mastering technologies, which are unable to produce optically flat vertical cavity walls in glass or plastic.

The refracted light obeys the law of refraction, i.e., $$RI_I \sin(A_I) = RI_R \sin(A_R)$$

where $RI_I$=first refractive index;
$A_I$=angle of incidence;
$RI_R$=second refractive index; and
$A_R$=angle of refraction.

As the polymer has a refractive index (approximately 1.41) less than the refractive index of glass (approximately 1.52), the angle of refraction is larger than the angle of incidence and the light bends further away from the normal to the boundary 106. Many light rays are lost due to light escaping 116 out of the detection cell instead of being trapped in the cavity by Fresnel reflection. This degrades the intensity of excitation light incident on the samples, which in turn adversely effects the detected signal strength. Furthermore, refracted light rays may also reflect 114 off the internal surfaces of the cavity 108 causing interference and detection signal loss. In other words, the curved or angled interfaces or boundaries in combination with the unfavorable refractive index change at the glass to polymer boundary or interface, leads to unsatisfactory light intensity and quality, leading to poor sample detection.

Moreover, the optical channels of these systems are often extended along a narrow tunnel to a dead end at the light receiving side of the detection cell. This introduces an interface, at the point where the tunnel meets the detection cell, that is hard to control, keep clean, and isolate from the high voltages in the detection cell. Further, the interface may cause a distortion of the electrophoresis field. Still further, bubbles trapped in the tunnel may optically interfere with the excitation light. This, in combination with poor light intensity and quality, further aggravates the signal detection.

In light of the above drawbacks, there is a need for an improved detection cell that provides better control over excitation light that is used to detect or analyze separated sample components that have been produced using techniques such as CE tube or microchip technology. Further, there is a need for an improved method for controlling the direction of the light rays within the detection cell.

SUMMARY OF THE INVENTION

According to the invention there is provided an energy beam guide. The energy beam guide comprises a first region having a first refractive index, the first region having an energy beam receiving end and an inclined first boundary opposing the energy beam receiving end. The energy beam guide also includes a second region having a second refractive index that is less than the first refractive index. The second region shares the first boundary with the first region, and has a declined second boundary opposing the first boundary. A predetermined distance separates the first and second boundaries. Finally, the energy beam guide comprises a third region having a third refractive index. The third region shares the second boundary with the second region.

Further according to the invention there is provided another energy beam guide. The energy beam guide comprises a first region having a first refractive index and a second region sharing an inclined first boundary with the first region. The second region has a second refractive index that is less than the first refractive index. The energy beam guide also includes a third region sharing a declined second boundary with the second region. The third region has a third refractive index. Also, a predetermined distance separates the first and second boundaries. The first refractive index is larger than the second refractive index, and preferably the second refractive index is larger than the third refractive index.

Still further according to the invention there is provided a detection cell, preferably part of an electrophoresis system. The detection cell comprises a substrate and first and second cavities formed in the substrate. The first cavity has a first cavity sloped wall and is configured to receive a first substance having a first refractive index. The substrate has a second refractive index. The second cavity has a second cavity sloped wall and is configured to receive a second substance having a third refractive index. A wall, defined by a region of the substrate, separates the first and second cavities from each other by a predetermined distance. The first refractive index is larger than the second refractive index, and preferably the second refractive index is larger than the third refractive index.

According to the invention there is also provided a method for making a detection cell. A substrate is firstly provided, where the substrate defines first and second cavities each having sloped walls and separated by a wall. The first cavity is filled with a first substance having a first refractive index. The substrate is made from a substance having a second refractive index. The second cavity is then filled with a second substance having a third refractive index. The first refractive index is larger than the second refractive index, and preferably the second refractive index is larger than the third refractive index.

Still further according to the invention there is provided a method for detecting component parts of a sample. A sample is firstly separated into its component parts by electrophoresis. An energy beam is directed at a first region having a first refractive index. The energy beam is then redirected towards a second boundary, where the redirecting occurs at an inclined first boundary separating the first region from a second region. The second region has a second refractive index. The energy beam is subsequently guided towards a third region that includes the component parts of the sample. The guiding occurs at a declined second boundary separating the second region from the third region. The component parts are then struck with the energy beam and energy emitted from the component parts is detected. Again, the first refractive index is larger than the second refractive index, and preferably the second refractive index is larger than the third refractive index. The redirecting and guiding steps comprise refracting the energy beam, such that at the boundaries an angle or refraction of the energy beam is larger than an angle of incidence.

The invention has a number of advantages over the prior art, for example:

1. The excitation energy beam is guided to a first boundary by total internal reflection.

2. The distance between the cavities or regions, and the indices of refraction can be adjusted to compensate for the detractive dispersion that occurs at an entry interface of the second cavity.

3. The distance between the cavities or regions provides a optical interface with the second cavity while isolating the optical path from the polymer, chemistry and a high voltage. The first cavity and its elements are not exposed to the high pressures required to refill the separation medium, i.e., the polymer in the second cavity.

4. The invention eliminates tunnels, which are filled with the separation medium and require special cleaning and refilling procedures to assure a clean optical interface and satisfactory bubble removal.

5. The second cavity is fabricated by the same process, and at the same time, as the first cavity. This assures proper alignment and consistent dimensions.

BRIEF DESCRIPTION OF THE DRAWINGS

For a better understanding of the nature and objects of the invention, reference should be made to the following detailed description, taken in conjunction with the accompanying drawings, in which.

Like reference numerals refer to corresponding parts throughout the several views of the drawings.

DETAILED DESCRIPTION OF THE PREFERRED EMBODIMENTS

To address the drawbacks of the prior art, a number of different embodiments were tested. Ray tracing was carried out based on ideal geometrical and theoretical models of light propagation. To fully describe the success of the preferred embodiments of the invention, the unsuccessful models are briefly described below in relation to FIGS. 1B and 1C.

Figure 1A:
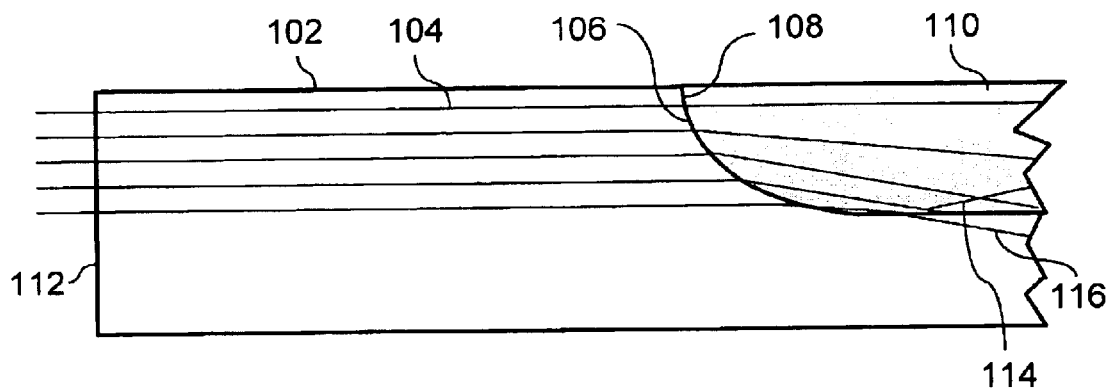
FIG. 1A is a partial cross-section of a prior art detection cell.
Figure 1B:
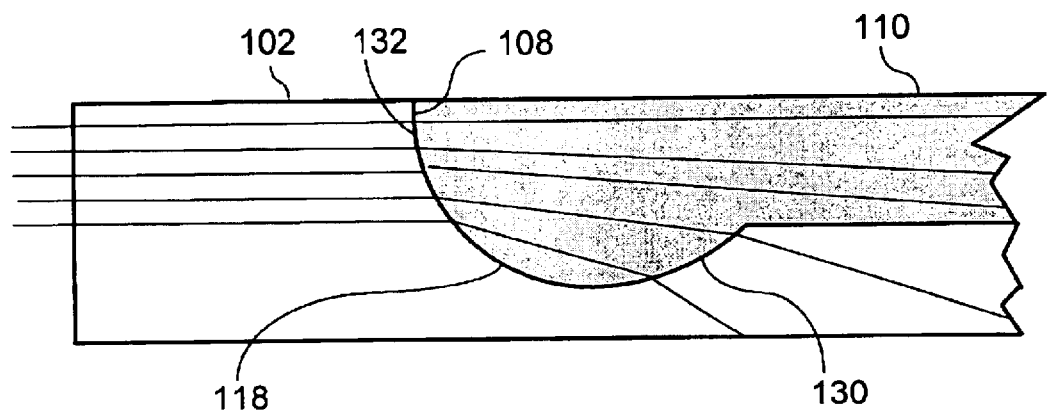
FIG. 1B is a detection cell having a blunted channel.

FIG. 1B shows a detection cell having a blunted channel 118 for attempting to address the above described drawbacks. Here, a blunted channel 118 is used to eliminate any interference created by internal reflection. Rays of light that might reflect off the internal surfaces of the cavity 108 are refracted at another boundary or interface 130 through an angle of reflection less than the angle of incidence. This bends the light rays further away from the cavity, avoiding internal reflection. Although this embodiment lessens interference effects associated with diffraction due to less curvature at a boundary 130, the intensity of the excitation light in the cavity is greatly diminished.

Figure 1C:
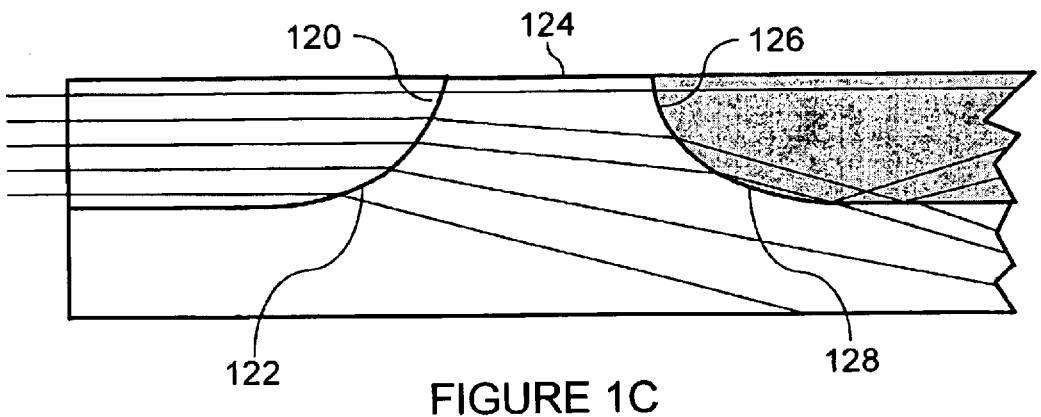
FIG. 1C is a detection cell with two cavities.

FIG. 1C shows a substrate 124 with two cavities. The substrate 124 is made from a material such as plastic or glass having a refractive index of approximately 1.52. The substrate 124 forms a first empty cavity 120 containing air with a refractive index of approximately 1.00. The substrate 124 also forms a second cavity 126 that is filled with a polymer having a refractive index of approximately 1.41. Obeying the law of refraction, the angle of refraction at a first boundary 122 between the air and the glass is less than the angle of incidence of the light passing through the boundary. This means that the light is refracted downward, as shown.

Those beams that pass through a second boundary 128 between the glass and the polymer are also refracted downward, as the angle of refraction is greater than the angle of incidence. Again, this embodiment lowers the intensity of the light in the second cavity 126, due to the fact that some light does not reach the second boundary 128.

Neither of the embodiments shown in FIGS. 1B nor FIG. 1C were found to sufficiently address the drawbacks of the prior art. In light of the above, the embodiments of the invention described below were developed. FIGS. 2 and 3 below show a system for controlling the excitation light according to a preferred embodiment of the invention.

Figure 2A:
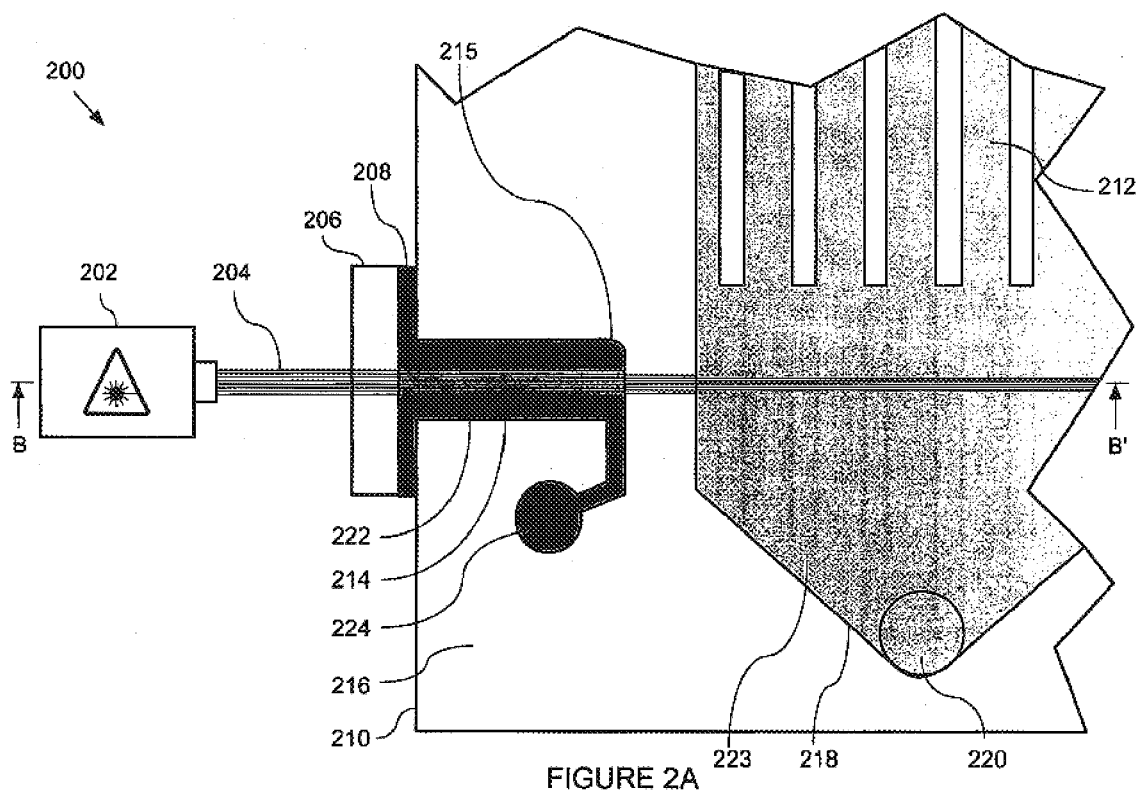
FIG. 2A is a partial top view of a capillary electrophoresis system according to an embodiment of the invention.
Figure 3:
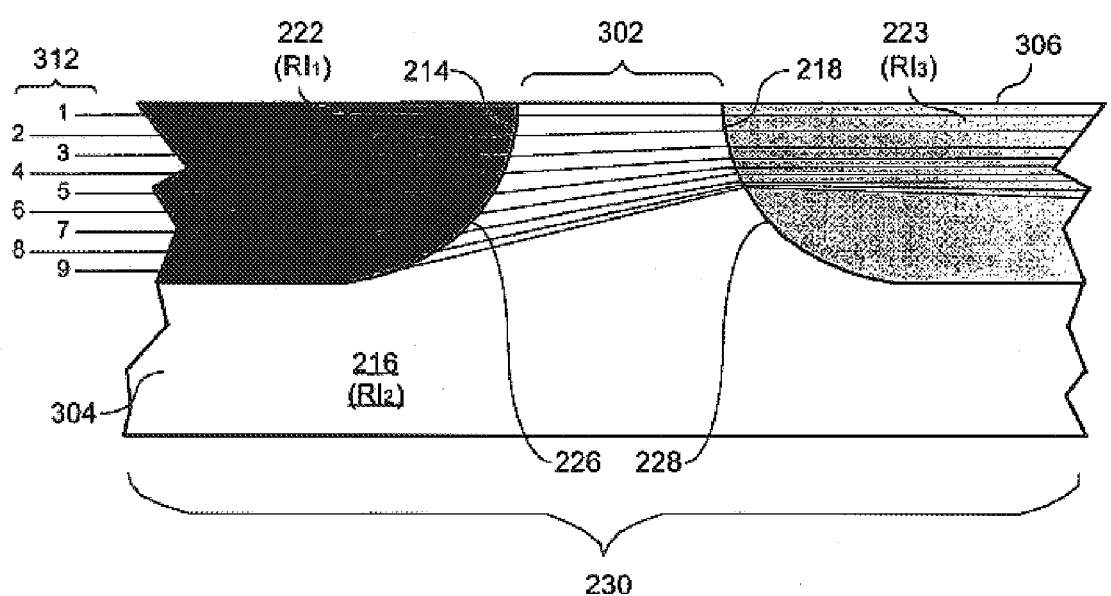
FIG. 3 is a enlarged view of part of FIG. 2B.

FIG. 2A is a partial top view of a CE system 200 according to an embodiment of the invention. The CE system 200 preferably comprises an excitation source 202, a detection cell 210, a first cavity 214, and a second cavity 218. The excitation source 202 is configured to emit an energy beam 204 at the detection cell 210. In a preferred embodiment, the excitation source 202 is an argon gas laser that emits excitation light. For convenience, the energy beam 204 will sometimes be referred to as the excitation light, although it should be appreciated that any suitable energy may be used.

The detection cell 210 comprises of a substrate 216 that forms a first cavity 214 and a second cavity 218. The first cavity 214 is preferably filled or cast with a first substance that is chosen for its ease of handling, adhesive properties, and optical properties, such as transparency and refractive index, hereafter known as the first refractive index ($RI_1$). In a preferred embodiment the first cavity 214 is filled with an optical adhesive or a fluid having the first refractive index, which has a refractive index of between approximately 1.47 and 1.61. An inlet 224 is preferably provided for filling the first cavity 214 with the first substance. The first cavity 214 is preferably considerably wider than the energy beam 204 to ensure that the beam does not come into contact with the rounded edges 215 on the sides of the first cavity 214.

The substrate 216 is preferably made from a second substance chosen for its ease of manufacture, and optical properties, such as transparency and refractive index, hereafter known as the second refractive index ($RI_2$). The second substance is any material through which light can propagate and that preferably has a refractive index in the range of 1.46 to 1.52. In a preferred embodiment the second substance is glass, which has a refractive index of approximately 1.52 or 1.472. This refractive index was chosen because there are many suitable plastics that have similar refractive indices and that may be substituted for the glass to lower costs.

The second cavity 218 contains a third substance 223 chosen for its ability to conduct electricity, hold samples in suspension, and its optical properties, such as transparency and refractive index, hereafter known as the third refractive index ($RI_3$). In a preferred embodiment, the third substance 223 is a polymer, which has a refractive index in the range of 1.33 to 1.46. In a preferred embodiment, the third refractive index is 1.41. In a preferred embodiment, the second cavity 218 is where the detection of a sample entrained in the third substance 223 is detected.

To achieve optimal intensity and quality of the excitation energy, the overall relationship between the refractive indices is preferably as follows:

$$RI_1 > RI_2 > RI_3$$

Capillaries or channels 212 open at their outlet ends into the second cavity 218 as described in the background section above. Another inlet 220 is preferably provided for filling the second cavity 218 with the third substance 223.

An optical element 206 is preferably coupled to the substrate 216 in the path of the energy beam 204. The optical element 206 is preferably an optical flat, such as a flat glass disc having very accurately polished surfaces, and is used to control the input optical surface. In a preferred embodiment, the optical element 206 is structurally bonded to the substrate 216 by an optical adhesive in the first cavity 214.

In one embodiment, the first cavity may be open on the energy beam receiving end of the substrate 216 nearest to the excitation source 202. In this embodiment where there is no wall separating the optical element from the first cavity, the optical element is easily affixed to the substrate 216. This is accomplished by placing the optical element adjacent the first cavity 214, filling the first cavity with adhesive, and allowing some adhesive to flow between the optical element and the substrate 216. When the adhesive dries, the optical element will have adhered to both the adhesive in the first cavity, and to the adhesive, which has leaked out of the first cavity 214 onto a sidewall of the substrate 216 bounding the first cavity 214. In the embodiment where a liquid index matching fluid is used, instead of an adhesive, the optical element may be bonded to the substrate 216 prior to the filling of the first cavity, or it may be held in place by an external support. Alternatively, no optical flat is necessary where the second substance in the first cavity is cast with an optically flat surface exposed to the excitation source.

Figure 2B:
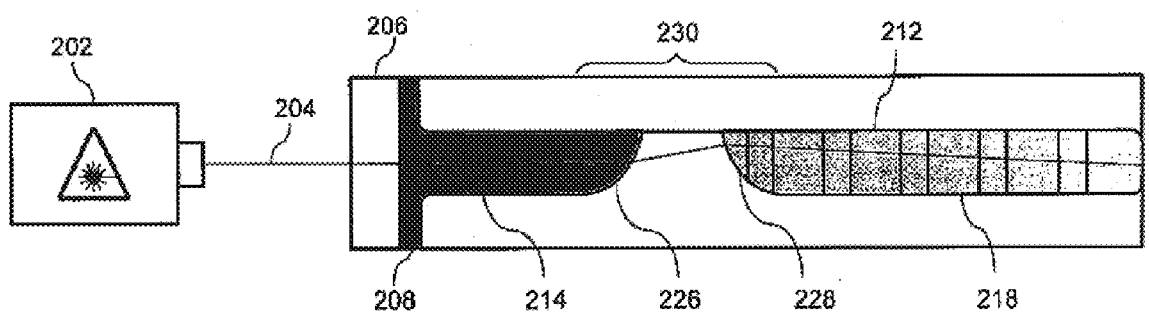
FIG. 2B is a cross-sectional side view of the capillary electrophoresis system shown in FIG. 2A, taken along line BB'.

FIG. 2B is a cross-sectional side view of the CE system shown in FIG. 2A, taken along line BB'. The side view clearly shows the first and second cavities 214 and 218, respectively. As described above, the cavities do not have rectilinear walls, but rather sloped or curved boundaries 226 and 228, due to the limitations of etching technologies currently available for glass and plastic masters. In a preferred embodiment, the first boundary 226 has an inclined or concave shape, while the second boundary has a declined or convex shape, as presented to the incident energy beam 204. This leads to a refraction of the energy beam 204 at the boundaries 226 and 228, as explained in relation to FIG. 3 below.

FIG. 3 is an enlarged view of portion 230 of FIG. 2B. To illustrate the light guiding principles of the invention, nine light rays 312 are shown passing through the first cavity 214, first boundary 226, substrate 216, second boundary 228, and second cavity 218, respectively. It should however be appreciated that any suitable energy beam may be used instead of the light rays. As described above, the first cavity 214 is filled with a first substance 222 having a first refractive index $RI_1$; the substrate 216 is made from a second substance 304 having a second refractive index $RI_2$; and the second cavity 218 is filled with a third substance 223 having a third refractive index $RI_3$. Also as described above, the substances 222, 304, and 223 are chosen so that $RI_1 > RI_2 > RI_3$. In other words, the first substance 222 contained by the first cavity 214 forms a first region, the third substance 223 contained in the second cavity 218 forms a third region, and the substrate 216 made from the second substance 304 forms a second region, which separates the first and second regions by a distance 302.

Light rays 1 and 2 pass through the first and second boundary 226 and a second boundary 228 normal to these boundaries. Therefore, little or no refraction occurs for these rays. Boundaries 226 and 228 typically have a curved shape, and, therefore, the angle of incidence of the light rays incident on these boundaries increases as the angle of the inclined slope increases. In other words, the angle of incidence of light ray 3 striking first boundary 226 is smaller than the angle of incidence of light ray 9 striking first boundary 226. Due to the orientation of the inclined slope of the first boundary 226, as well as the fact that $RI_1$ is larger than $RI_2$, the angle of refraction will be larger than the angle of incidence at the first boundary 226, thereby bending the light rays upward. Similarly, due to the orientation of the declined slope of the second boundary 228, as well as the fact that $RI_2$ is larger than $RI_3$, the angle of refraction will also be larger than the angle of incidence at the second boundary 228, thereby bending the light rays downward. In other words, the incline or decline boundaries effectively determine whether the light is bent upwards or downwards. The cumulative effect of both surfaces is to result in an exiting light ray that is as parallel to the channel surface 306 as possible. Furthermore, the distance 302 between the first and second boundaries 226 and 228 respectively, affects the path of the light rays, specifically how close the rays of light remain to each other.

It should be noted that boundaries 226 and 228 are contiguous. No other substance forms a layer between each region at the boundary, i.e, there is no air or other substance, such as adhesive, separating the regions from one another.

Furthermore, because $RI_1$ is preferably larger than $RI_2$, any light in the first cavity 214 is reflected inside the channel by total internal reflection. Because $RI_3$ is preferably less than $RI_2$, any reflection that occurs within the second cavity 218 is due to Fresnel reflection. Fresnel reflection is only 80% efficient where the angle of incidence of incident light, is larger than 89 degrees, i.e., the beam angle is within 1 degrees of the reflecting surface.

Therefore, by selecting the refractive indices $RI_1$, $RI_2$, and $RI_3$, and the distance 302 between the boundaries 226 and 228, the energy beam (e.g. light rays) can be accurately guided through the detection cell. This retains the intensity of light in the second cavity 218 and reduces the amount of internal reflection by reducing the amount of light lost to rays that exceed the Fresnel reflection angle, which is less than 2 degrees for a 90% efficiency reflection. In a preferred embodiment, the distance 302 is between 0.1 and 1000 microns.

Figure 4A:
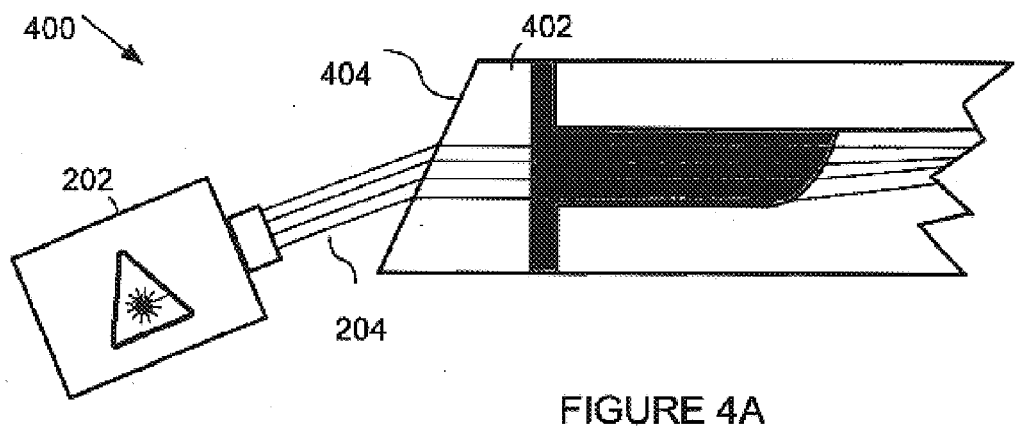
FIG. 4A is a partial cross-sectional side view of a capillary electrophoresis system incorporating a different optical element, according to another embodiment of the invention.

FIG. 4A is a partial cross-sectional side view of a CE system 400 incorporating a different optical element 402, according to another embodiment of the invention. The entry surface 404 of the optical element 402 is angled to facilitate an energy beam 204 that strikes the optical element at an angle, and may improve fabrication by allowing for draft, which is the angle allowed on component sides to facilitate component removal from a mold, i.e., injection molded optics.

Figure 4B:
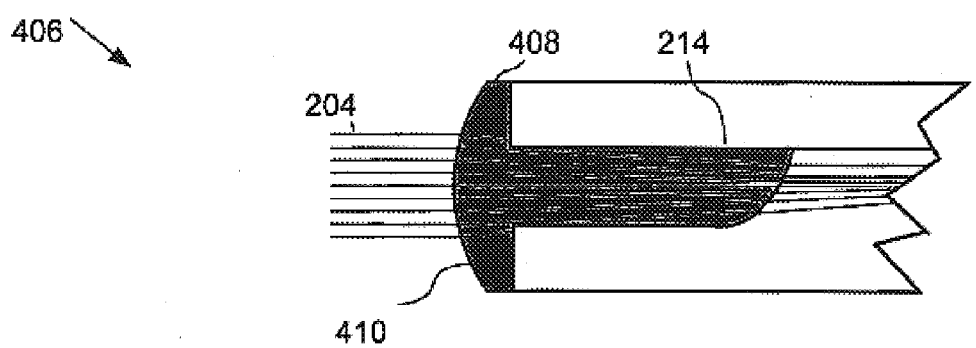
FIG. 4B is a partial cross-sectional side view of a capillary electrophoresis system incorporating another optical element, according to yet another embodiment of the invention.

FIG. 4B is a partial cross-sectional side view of a CE system 406 incorporating another optical element 408, according to yet another embodiment of the invention. The optical element 408 is preferably cast from, and at the same time as, the first substance 222 (FIG. 2) is cast into the first cavity 214. The cast optical element 408 may be cast in any suitable shape, but is preferably cast as a cylindrical lens that focuses the energy beam 204 into the first cavity 214.

Figure 4C:
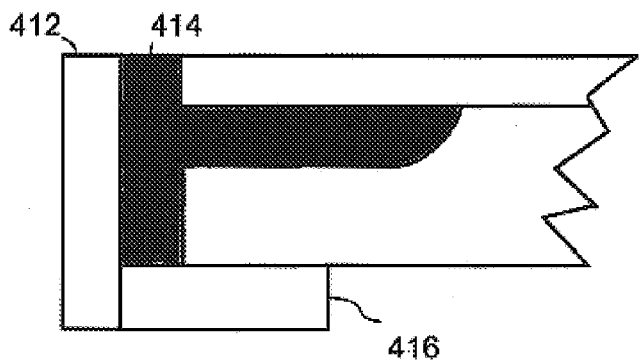
FIG. 4C is a partial cross-sectional side view of a capillary electrophoresis system incorporating an optical element and a support block, according to yet another embodiment of the invention.

FIG. 4C is a partial cross-sectional side view of a capillary electrophoresis system incorporating an optical element and a support block, according to yet another embodiment of the invention. This embodiment allows for the first substance to be a liquid, such as an index matching fluid. In this embodiment a support block 416 is used to support and align an optical element 412. The support block 414 forms a lower floor of a first cavity holding a first substance from which the first region 414 is composed. The support block 414 is preferably made from a plastic, glass, or ceramic.

The portion of the system not shown in FIGS. 4A, 4B, and 4C is the same as that shown and described in relation to FIGS. 2 and 3 above.

Figure 5A:
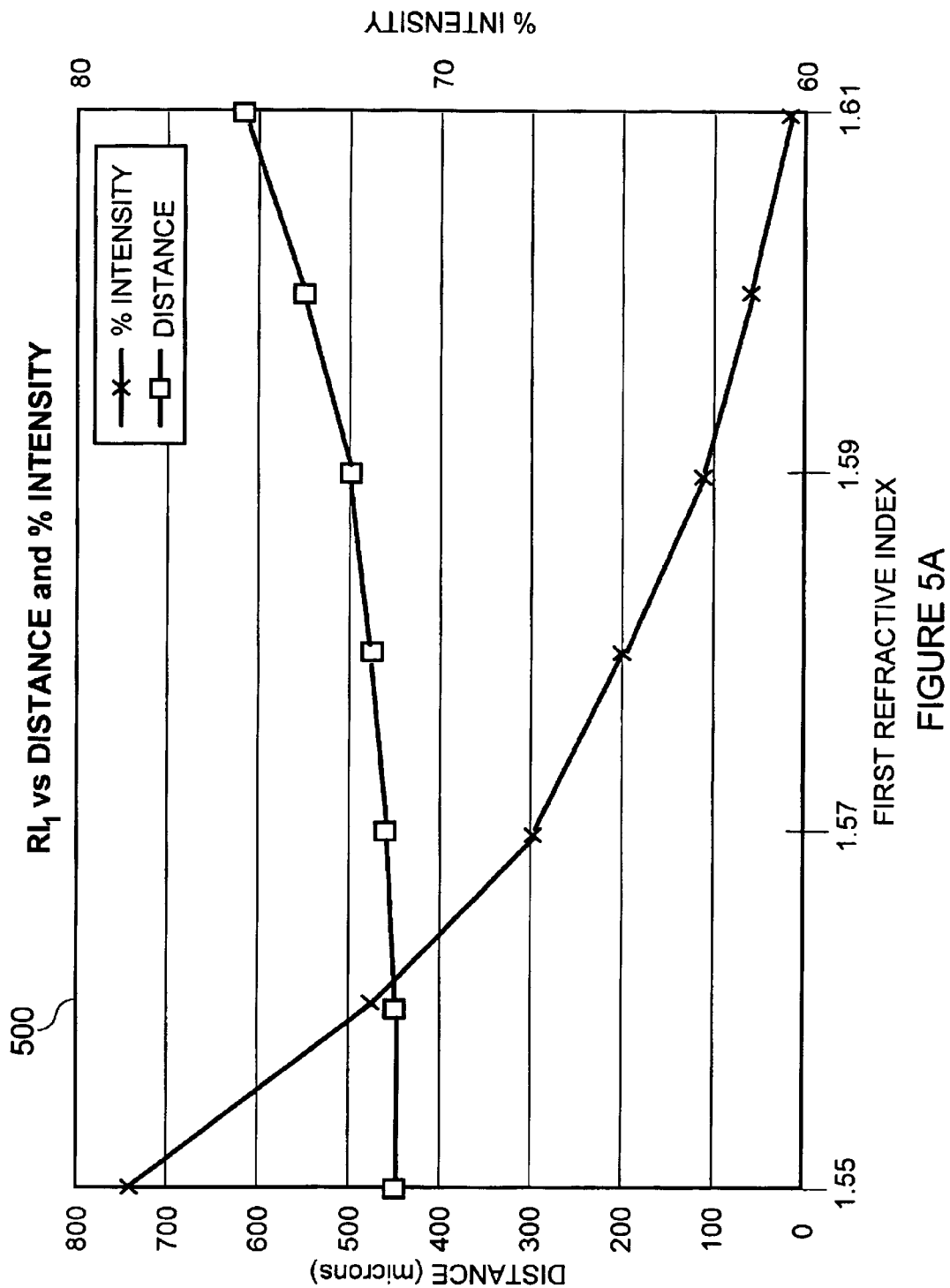
FIG. 5A is a graph of "$RI_1$ vs DISTANCE and % INTENSITY" according to an embodiment of the invention.

FIG. 5A is a graph 500 of "RI$_1$ vs DISTANCE and % INTENSITY" according to an embodiment of the invention. "DISTANCE" refers to the distance 302 (FIG. 3) between the first boundary 226 (FIG. 3) and the second boundary 228 (FIG. 3) at their closest distance to one another, i.e, measured along the shortest possible segment separating them. "FIRST REFRACTIVE INDEX" refers to the first refractive index (RI$_1$), while "% INTENSITY" refers to the percentage intensity of the energy beam at approximately 17 mm into the second cavity (third region) 218 (FIG. 3) from the second boundary, as measured in a direction away from the first and second regions. As can be seen, the % Intensity increases by a few percentage points for larger first refractive indices (RI$_1$), while the gap can be made significantly smaller by increasing the first refractive index (RI$_1$). Therefore, a small gap with a high first refractive index (RI$_1$) is preferred. In this embodiment, the preferred substances 222, 304, and 223 (FIG. 3) are as follows: first substance 222 (FIG. 3) is an adhesive made by ABLESTIK, MASTERBOND, or NYE OPTICAL having a first refractive index in the range of 1.56 to 1.57 inclusive; second substance 304 (FIG. 3) is 0211 CORNING GLASS (made by CORNING) having a second refractive index of 1.52, or a ZEONOR 1020R plastic having a second refractive index of 1.523; and third substance 223 (FIG. 3) is APPLIED BIOSYSTEMS POP-6 POLYMER GEL MATRIX having a third refractive index of 1.41. The refractive index of the optical element is both unknown and unimportant.

Figure 5B:
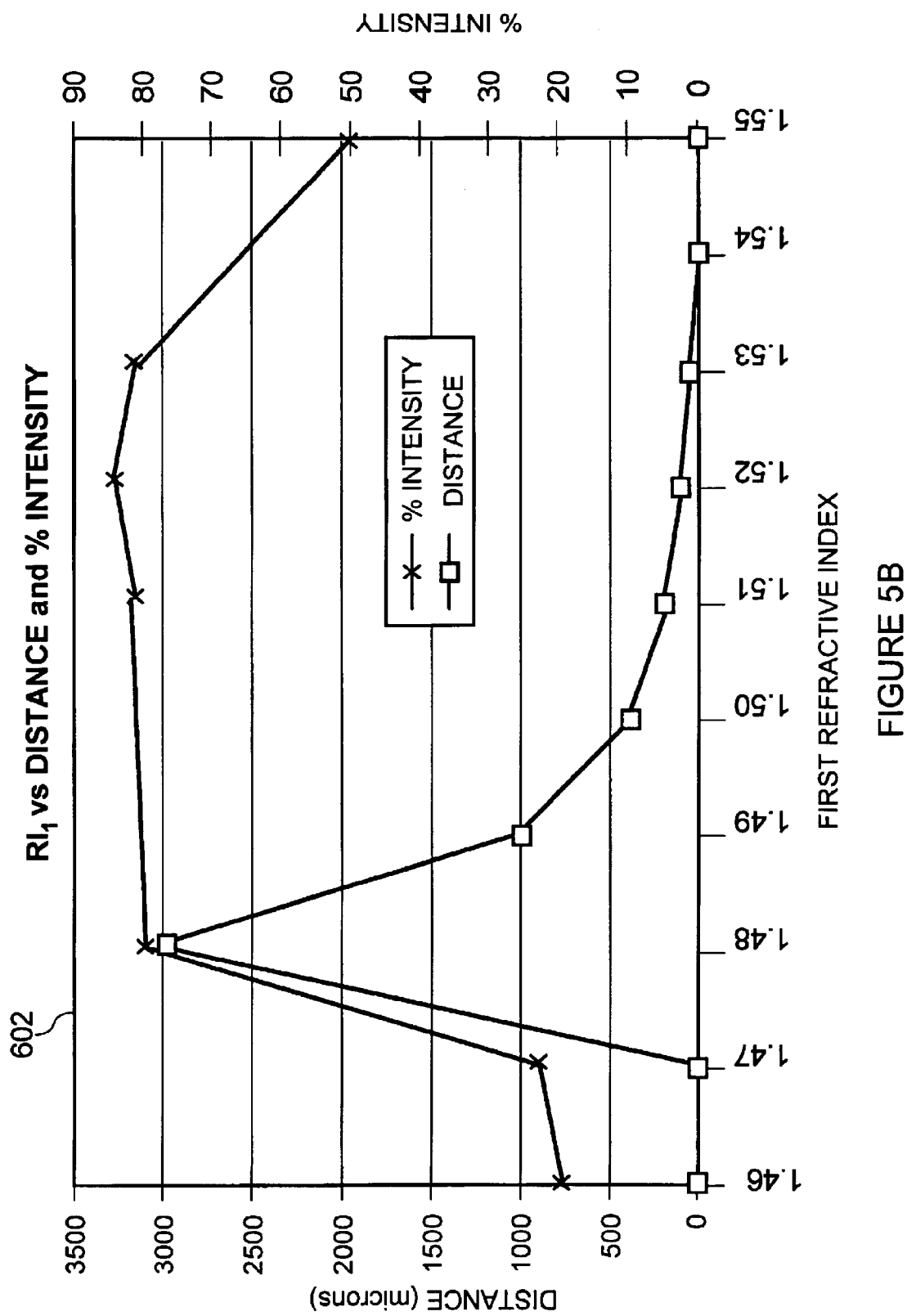
FIG. 5B is another graph of "$RI_1$ vs DISTANCE and % INTENSITY" according to another embodiment of the invention.

FIG. 5B is another graph 502 of "RI1 vs DISTANCE and % INTENSITY" according to another embodiment of the invention. This chart is similar to that shown in FIG. 5A. The chart shows that for an intensity above 0%, the first refractive index (RI$_1$) must lie in the range of 1.47 to 1.52 inclusive, a suitable intensity and distance occurring at an RI$_1$ of about 1.50, and a distance of 420 microns. The highest intensity occurs at approximately 30 microns, but this distance is too small for manufacturing processing purposes. In this embodiment, the preferred substances 222, 304, and 223 (FIG. 3) are as follows: first substance 222 (FIG. 3) is CARGILLE LIQUID INDEX MATCH fluid (made by CARGILLE LABORATORIES, Inc.) having a first refractive index of 1.50; second substance 304 (FIG. 3) is BOROFLOAT GLASS (made by SCHOTT GLASS) having a second refractive index of 1.472; and third substance 223 (FIG. 3) is POP-6 POLYMER GEL MATRIX (made by APPLIED BIOSYSTEMS) having a third refractive index of 1.41. The refractive index of the optical element is both unknown and unimportant, although a suitable optical element may be a VWR 48393-070 (made by VWR Scientific Products).

One skilled in the art will appreciate that once the first substance and the second substance are selected, selections of a suitable distance 302 (FIG. 3) and a suitable first refractive index (RI$_1$) may be made by utilizing graph 500.

Figure 6A:
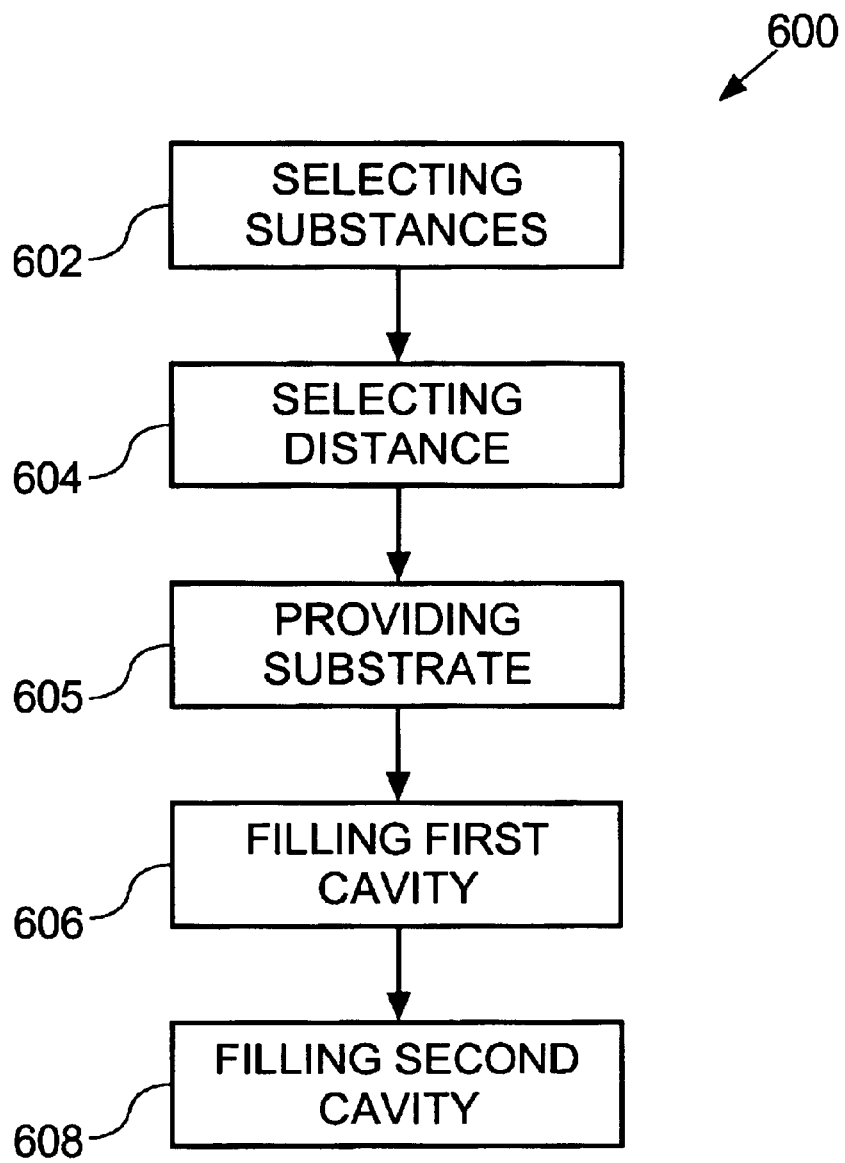
FIG. 6A is a flow chart of a method for guiding an energy beam in an electrophoresis system, according to an embodiment of the invention.

FIG. 6A is a flow chart 600 of a method making an energy beam guide, according to an embodiment of the invention. First, second, and third substances are initially selected (at 602), such that RI$_1$ is larger than RI$_2$, which is larger than RI$_3$. In a preferred embodiment, RI$_3$ is available in a narrow range of indices. RI$_2$ is selected as the substrate and RI$_1$ is determined based on RI$_2$ and RI$_3$ from charts, iterative calculations, from a model, or through experimentation. The distance or wall between the first and second cavities is then selected (at 604). A substrate is provided (at 605) and defines first and second cavities each having sloped walls and separated by a wall. The substrate is made from the second substance which has a second refractive index (RI$_2$). The first cavity is filled (at 606) with a first substance having the first refractive index (RI$_1$). The second cavity is filled (at 608) with a second substance having the third refractive index (RI$_3$).

Figure 6B:
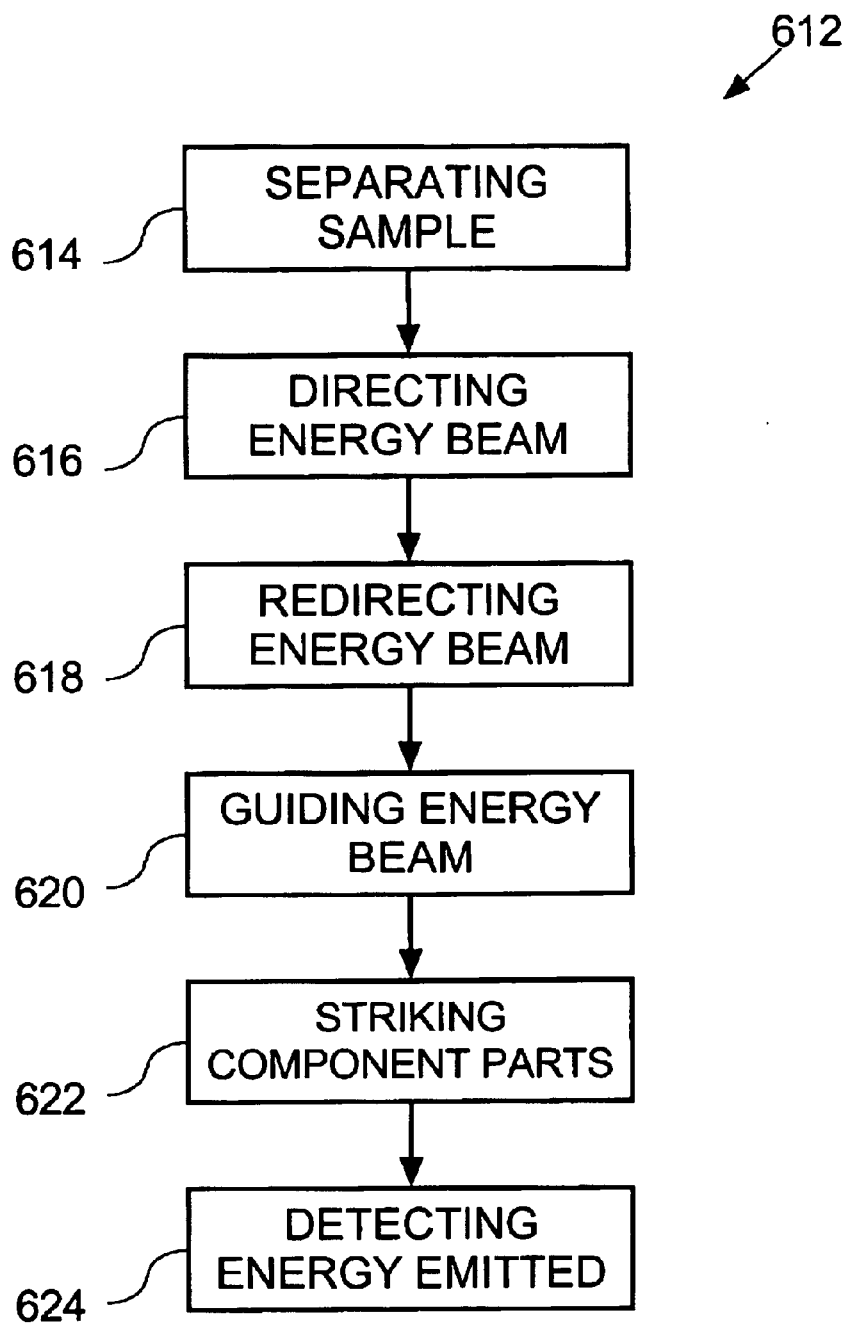
FIG. 6B is another flow chart of a method for guiding an energy beam in an electrophoresis system, according to another embodiment of the invention.

FIG. 6B is a flow chart 612 a method for detecting component parts of a sample, comprising. Initially, a sample is separated (at 614) into its component parts by electrophoresis. An energy beam is then directed (at 616) at a first region having a first refractive index (RI$_1$). The energybeam is subsequently redirected (at 618) towards a second boundary, where the redirecting occurs at an inclined first boundary separating the first region from a second region having a second refractive index. The energy beam is then guided (at 620) towards a third region that includes component parts of a sample. The guiding occurs at a declined second boundary separating the second region from the third region. The component parts are subsequently struck (at 622) with the energy beam. Finally, energy emitted from the component parts is detected (at 624). The first refractive index (RI$_1$) is larger than the second refractive index (RI$_2$), and the second refractive (RI$_2$) index is larger than the third refractive index (RI$_3$).

In the above described embodiments, where RI$_1$>RI$_2$>RI$_3$, optimal illumination is provided by directing the energy beam as parallel to the cavity surface 306 (FIG. 3) as possible, thereby, reducing the amount of reflections in the cavities. In an alternative embodiment, however, RI$_1$>RI$_2$>RI$_3$. In this embodiment, where the second refractive index is less than the third refractive index, light entering the third cavity is internally reflected by total internal reflection. This allows the embodiment to function through bouncing illumination. This embodiment, however, necessitates locating a suitable polymer with a refractive index greater than the substrate's refractive index.

The foregoing descriptions of specific embodiments of the present invention are presented for purposes of illustration and description. They are not intended to be exhaustive or to limit the invention to the precise forms disclosed, obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. Furthermore, the order of steps in the method are not necessarily intended to occur in the sequence laid out. It is intended that the scope of the invention be defined by the following claims and their equivalents.

What is claimed is:

1. An energy beam guide, comprising:
   a first region having a first refractive index, said first region having an energy beam receiving end and an first boundary opposing said energy beam receiving end;
   a second region having a second refractive index that is less than said first refractive index, said second region sharing said first boundary with said first region, and having a second boundary opposing said first boundary, where a predetermined distance separates said first and second boundaries; and
   a third region having a third refractive index, said third region sharing said second boundary with said second region;
   wherein said first boundary slopes upward and away from said energy beam receiving end, and said second boundary slopes downward and away from said eneray beani receiving end.

2. The energy beam guide of claim 1, wherein said second refractive index is larger than said third refractive index.

3. The energy beam guide of claim 1, wherein said second refractive index is less than said third refractive index.

4. The energy beam guide of claim 1, wherein said energy beam guide forms part of a detection cell of an electrophoresis system.

5. The energy beam guide of claim 4, wherein said third region defines a detection portion of said detection cell.

6. The energy beam guide of claim 1, further comprising an excitation source and a detector.

7. The energy beam guide of claim 1, wherein said first refractive index is in a range from 1.47 to 1.61.

8. The energy beam guide of claim 1, wherein said second refractive index is in a range from 1.46 to 1.52.

9. The energy beam guide of claim 1, wherein said second refractive index is 1.52.

10. The energy beam guide of claim 1, wherein said second refractive index is 1.472.

11. The energy beam guide of claim 1, wherein said third refractive index is is in a range from 1.33 to 1.46.

12. The energy beam guide of claim 1, wherein said third refractive index is 1.41.

13. The energy beam guide of claim 1, wherein said first region is an optical adhesive.

14. The energy beam guide of claim 1, wherein said first region is a liquid index matching fluid.

15. The energy beam guide of claim 1, wherein said second region is selected from a group consisting of glass and plastic.

16. The energy beam guide of claim 1, wherein said third region is a migration medium.

17. The energy beam guide of claim 16, wherein said migration medium is a polymer.

18. The energy beam guide of claim 1, wherein said inclined first boundary presents a concave shape to said energy beam.

19. The energy beam guide of claim 1, wherein said declined second boundary presents a convex shape to said energy beam.

20. The energy beam guide of claim 1, wherein said energy beam is refracted at said first and second boundaries.

21. The energy beam guide of claim 20, wherein an angle of refraction is greater than the angle of incidence at both said first and second boundaries.

22. The energy beam guide of claim 1, wherein a shortest distance separating said first region from said second region is in a range from 0.1 to 1000 microns.

23. The energy beam guide of claim 1, further comprising an optical element disposed between an energy beam source and said energy beam guide.

24. The energy beam guide of claim 23, wherein an energy beam receiving end of said optical element is sloped.

25. The energy beam guide of claim 23, wherein said optical element is formed from a substance that comprises said first region.

26. An energy beam guide, comprising:
a first region having a first refractive index;
a second region sharing an first boundary with said first region, said second region having a second refractive index that is less than said first refractive index; and
a third region sharing a second boundary with said second region, said third region having a third refractive index, where a predetermined distance separates said first and second boundaries;
wherein said first boundary slopes upward and away from said energy beam receiving end, and said second boundary slopes downward and away from said energy beam receiving end.

27. The energy beam guide of claim 26, wherein said second refractive index is larger than said third refractive index.

28. The energy beam guide of claim 26, wherein said second refractive index is less than said third refractive index.

29. The energy beam guide of claim 26, wherein said energy beam guide forms part of a detection cell of an electrophoresis system.

30. The energy beam guide of claim 29, wherein said third region defines a detection portion of said detection cell.

31. The energy beam guide of claim 26, further comprising an excitation source and a detector.

32. The energy beam guide of claim 26, wherein said first refractive index is in a range from 1.47 to 1.61.

33. The energy beam guide of claim 26, wherein said second refractive index is in a range from 1.46 to 1.52.

34. The energy beam guide of claim 26, wherein said second refractive index is 1.52.

35. The energy beam guide of claim 26, wherein said second refractive index is 1.472.

36. The energy beam guide of claim 26, wherein said third refractive index is in a range from 1.33 to 1.46.

37. The energy beam guide of claim 26, wherein said third refractive index is 1.41.

38. The energy beam guide of claim 26, wherein said first region is an optical adhesive.

39. The energy beam guide of claim 26, wherein said first region is a liquid index matching fluid.

40. The energy beam guide of claim 26, wherein said second region is selected from a group consisting of glass and plastic.

41. The energy beam guide of claim 26, wherein said third region is a migration medium.

42. The energy beam guide of claim 41, wherein said migration medium is a polymer.

43. The energy beam guide of claim 26, wherein said inclined first boundary presents a concave shape to an energy beam.

44. The energy beam guide of claim 26, wherein said declined second boundary presents a convex shape to an energy beam.

45. The energy beam guide of claim 26, wherein an energy beam is refracted at said first and second boundaries.

46. The energy beam guide of claim 45, wherein an angle of refraction is greater than the angle of incidence at both said first and second boundaries.

47. The energy beam guide of claim 26, wherein a shortest distance separating said first region from said second region is in a range from 0.1 to 1000 microns.

48. The energy beam guide of claim 26, further comprising an optical element disposed between an energy beam source and said energy beam guide.

49. The energy beam guide of claim 48, wherein an energy beam receiving end of said optical element is sloped.

50. The energy beam guide of claim 48, wherein said optical element is formed from a substance that comprises said first region.

* * * * *

UNITED STATES PATENT AND TRADEMARK OFFICE
CERTIFICATE OF CORRECTION

PATENT NO. : 6,731,437 B2  Page 1 of 1
DATED : May 4, 2004
INVENTOR(S) : Albert L. Carrillo It is certified that error appears in the above-identified patent and that said Letters Patent is hereby corrected as shown below:

Column 10,
Line 53, "end and an first" should read -- end and a first --.
Line 66, "eneray" should read -- energy --.
Line 67, "beani" should read -- beam --.

Column 11,
Line 21, "index is is in" should read -- index is in --.
Line 59, "sharing an first" should read -- sharing a first --.

Signed and Sealed this

Second Day of May, 2006

JON W. DUDAS
*Director of the United States Patent and Trademark Office*